US008642022B2

(12) United States Patent
Falk et al.

(10) Patent No.: US 8,642,022 B2
(45) Date of Patent: *Feb. 4, 2014

(54) COPOLYMERS OF EPOXY COMPOUNDS AND AMINO SILANES

(75) Inventors: Benjamin Falk, Yorktown Heights, NY (US); Anne Dussaud, Tarrytown, NY (US); Lara P. Fieschi-Corso, Danbury, CT (US)

(73) Assignee: Momentive Performance Materials Inc., Waterford, NY (US)

( * ) Notice: Subject to any disclaimer, the term of this patent is extended or adjusted under 35 U.S.C. 154(b) by 406 days.

This patent is subject to a terminal disclaimer.

(21) Appl. No.: 12/740,296

(22) PCT Filed: Oct. 30, 2008

(86) PCT No.: PCT/US2008/012291
§ 371 (c)(1),
(2), (4) Date: Apr. 28, 2010

(87) PCT Pub. No.: WO2009/061360
PCT Pub. Date: May 14, 2009

(65) Prior Publication Data
US 2010/0310491 A1 Dec. 9, 2010

Related U.S. Application Data

(63) Continuation-in-part of application No. 12/260,169, filed on Oct. 29, 2008, now abandoned.

(60) Provisional application No. 60/984,753, filed on Nov. 2, 2007.

(51) Int. Cl.
*A61Q 5/12* (2006.01)
*A61K 9/00* (2006.01)
*A61K 31/74* (2006.01)
*A61K 8/00* (2006.01)
*A61Q 5/00* (2006.01)
*C08G 77/04* (2006.01)

(52) U.S. Cl.
USPC ............... 424/70.122; 424/70.11; 424/70.12; 424/70.1; 424/78.08; 424/400; 528/34

(58) Field of Classification Search
USPC ........... 424/70.122, 70.11, 70.12, 78.08, 400; 528/34
See application file for complete search history.

(56) References Cited

U.S. PATENT DOCUMENTS

| 3,449,281 A | 6/1969 | Sullivan et al. |
| 3,980,599 A * | 9/1976 | Kondo et al. ............ 106/287.11 |
| 2003/0177590 A1 | 9/2003 | Rollat-Corvol et al. |
| 2007/0106045 A1 | 5/2007 | Lange et al. |
| 2009/0117793 A1* | 5/2009 | Falk et al. ........................ 442/59 |
| 2011/0020627 A1* | 1/2011 | Falk et al. ..................... 428/221 |
| 2011/0021096 A1* | 1/2011 | Falk ............................... 442/59 |
| 2011/0044934 A1* | 2/2011 | Falk ........................... 424/78.38 |
| 2011/0127195 A1* | 6/2011 | Koczo et al. .................. 208/291 |

FOREIGN PATENT DOCUMENTS

| CA | 866 244 A | 3/1971 |
| CN | 1488677 A | 4/2004 |
| WO | WO03066007 A1 | 8/2003 |
| WO | WO 2006067225 A1 * | 6/2006 |

* cited by examiner

*Primary Examiner* — Abigail Fisher
(74) *Attorney, Agent, or Firm* — Dominick G. Vicari; Joseph S. Ostroff

(57) ABSTRACT

The present invention provides for a personal care composition suitable for treating hair comprising a composition comprising the reaction product of a) an oxirane or oxetane compound comprising at least two oxirane or oxetane groups; and b) an amino silane having the formula: $N(H)(R^1)R^2Si(OR^3)_{3-a-b-c}(OR^4)_a(R^5Si(OR^6)d(R^7)_c)_bR^8_c$ with $R^1$ is chosen from the group consisting of H or a monovalent hydrocarbon radical containing one to 20 carbon atoms; $R^2$ is selected from a group consisting of a divalent linear or branched hydrocarbon radical consisting of 1-60 carbons; $R^4$ is a hydrocarbon radical that contains 3 to 200 carbon atoms; $R^5$ is selected from a group consisting of oxygen or a divalent linear or branched hydrocarbon radical consisting of 1-60 carbons; $R^3$, $R^6$, $R^7$, and $R^8$ and are each independently selected from the group of monovalent linear or branched hydrocarbon radicals having from 1 to 200 carbon atoms; the subscript b is zero or a positive number and has a value ranging from 0 to 3; the subscripts a is zero or appositive number less than 3, the subscripts b and c are zero or positive and have a value ranging from 0 to 3 subject to the limitation that (a+b+c)<3; the subscripts d and e are zero or positive and have a value ranging from 0 to 3 subject to the limitation that (d+e)=3, wherein when hair is treated with said personal care composition said hair has a hydrophobic response to water.

40 Claims, No Drawings

COPOLYMERS OF EPOXY COMPOUNDS AND AMINO SILANES

CROSS-REFERENCE TO RELATED APPLICATION PAPERS

This application is a national phase application of PCT/US2008/12291 filed on Oct. 30, 2008, which claims priority to U.S. Provisional Application No. 60/984,753 filed Nov. 2, 2007, and which is a continuation in part of U.S. application Ser. No. 12/260,169 filed Oct. 29, 2008, now abandoned.

FIELD OF THE INVENTION

The present invention relates to novel copolymers formed as the reaction product of epoxy compounds and amino silanes.

BACKGROUND OF THE INVENTION

Modified silicones can exhibit a variety of physical properties. The polymers can be modified to be hydrophilic, lipophilic and hydrophobic depending on the nature of the organic substituents. Recently, linear alternating copolymers and linear random copolymers have been made using alkyl or polyether, and polydimethylsiloxane units. These materials have shown utility in a variety of applications including personal care (hair conditioners, skin care and color cosmetics), textile treatments, hard surface modifiers, agricultural adjuncts, and the like. Unfortunately these materials are liquids and show limited durability when applied to a surface.

U.S. Pat. No. 4,062,999 A describes a process for treating textile fibers with a mixture of an amino functional silane and an epoxy functional silicone. The unreacted mixture is applied to the fiber then heat-treated in an oven.

U.S. Pat. No. 4,359,545 A describes the process of reacting an amino functional silicone and an epoxy functional silicone onto a textile surface. The blend is applied to a textile then heat-treated in an oven.

U.S. Pat. No. 5,384,340 describes the use of a moisture and or photo curable coatings system. The process involves first reacting an epoxy or methacryl functional silane with an excess of an amino functional silicone. The remaining unreacted amino groups are then reacted with an epoxy or isocyano functional vinyl containing molecule. The resulting material contains both moisture curable alkoxy silane groups and free radical curable vinyl groups.

EP 1,116,813 A1 describes a textile treatment composition containing siloxanes having epoxy- and glycol-functionalities and either an aminosilane or a silicone quaternary ammonium compound. The composition is preferably formulated as an aqueous emulsion. The emulsion is applied to the textile surface followed by heat treatment to cure the mixture.

U.S. Pat. No. 5,102,930 A describes a silicone-based fabric finishing agent that is suitable for finishing a fabric material containing keratinous fibers, e.g., wool. The fabric finishing agent is an aqueous emulsion of a hydroxy-containing organopolysiloxane with an admixture of a mixture of colloidal silica and a reaction product of an amino-functional alkoxy silane or a hydrolysis product thereof with an acid anhydride, an epoxy-functional alkoxy silane compound and a curing catalyst.

U.S. Pat. No. 6,475,568 B1 describes the synthesis of non-crosslinkable silicone polyether non-(AB)n materials that do not contain silane or reactive groups. Durable films leaving the hair hydrophobic have been disclosed in WO 98/54255. This durability was achieved by crosslinking of copolymer which are silane modified polymethacrylate or acrylate. The application methods for hair treatment consists of keeping the copolymers away from water before use to prevent premature cross-linking. The hydrolyzing step required to allow the cross-linking process has to be performed shortly before use, which is not very convenient for the hair care product end-user.

US 2003/0177590 discloses an aqueous dispersion of particle where the reactive silyl function is protected by an acrylic polymer casing, and can be used directly on the hair. Other durable films on hair fiber described in U.S. Pat. No. 6,923,953 involve reducing the sulfur bonds of hair keratin and reacting active compounds on one or more reduced hair sulfur bond. WO 03/078503 describes the preparation of protein/silane copolymer, which can improve the flexabrasion properties of hair. More simple or method of treatments that do not involving a reducing step, would be useful.

SUMMARY OF THE INVENTION

The present invention provides for a composition comprising the reaction product of
a) an oxirane or oxetane compound comprising at least two oxirane or oxetane groups; and
b) an amino silane having the formula:

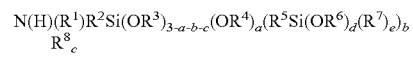

with $R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscript b is zero or a positive number and has a value ranging from 0 to 3;
the subscripts a is zero or appositive number less than 3, the subscripts b and c are zero or positive and have a value ranging from 0 to 3 subject to the limitation that $(a+b+c) \leq 3$;
the subscripts d and e are zero or positive and have a value ranging from 0 to 3 subject to the limitation that $(d+e)=3$, wherein when hair is treated with said personal care composition said hair has a hydrophobic response to water or wherein when human skin is with said personal care composition said skin exhibits an enhanced response to water.

DETAILED DESCRIPTION OF THE INVENTION

The present invention provides for a composition comprising the reaction product of
a) an oxirane or oxetane compound comprising at least two oxirane or oxetane groups; and
b) an amino silane having the formula:

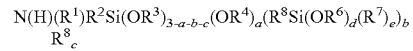

with $R^1$ is chosen from the group consisting of H or a monovalent hydrocarbon radical containing one to 20 carbon atoms;

$R^2$ is selected from a group consisting of a divalent linear or branched hydrocarbon radical consisting of 1-60 carbons;

$R^4$ is a hydrocarbon radical that contains 3 to 200 carbon atoms;

$R^5$ is selected from a group consisting of oxygen or a divalent linear or branched hydrocarbon radical consisting of 1-60 carbons;

$R^3$, $R^6$, $R^7$, and $R^8$ and are each independently selected from the group of monovalent linear or branched hydrocarbon radicals having from 1 to 200 carbon atoms;

the subscript b is zero or a positive number and has a value ranging from 0 to 3;

the subscripts a is zero or appositive number less than 3, the subscripts b and c are zero or positive and have a value ranging from 0 to 3 subject to the limitation that (a+b+c)≤3;

the subscripts d and e are zero or positive and have a value ranging from 0 to 3 subject to the limitation that (d+e)=3, wherein when hair is treated with said personal care composition said hair has a hydrophobic response to water or wherein when human skin is with said personal care composition said skin exhibits an enhanced response to water.

The present invention further provides for such reaction product compositions where the oxirane or oxetane compound is selected from the group consisting of siloxanes, hydrocarbons and polyethers particularly where the oxirane or oxetane compound is a siloxane having the formula:

$$M_j M^E_h M^{PE}_i M^H_j D_k D^E_l D^{PE}_m D^H_n T_o T^E_p T^{PE}_q T^H_r Q_s$$

with $M = R^9 R^{10} R^{11} SiO_{1/2}$;
$M^H = R^{12} R^{13} H SiO_{1/2}$;
$M^{PE} = R^{12} R^{13} (-CH_2 CH(R^{14})(R^{15})_t O(R^{16})_u (C_2H_4O)_v (C_3H_6O)_w (C_4H_8O)_x R^{17}) SiO_{1/2}$;
$M^E = R^{12} R^{13} (R^E) SiO_{1/2}$
$D = R^{18} R^{19} SiO_{2/2}$; and
$D^H = R^{20} H SiO_{2/2}$
$D^{PE} = R^{20} (-CH_2 CH(R^{14})(R^{15})_t O(R^{16})_u (C_2H_4O)_v (C_3H_6O)_w (C_4H_8O)_x R^{17}) SiO_{2/2}$
$D^E = R^{20} R^E SiO_{2/2}$.
$T = R^{21} SiO_{3/2}$;
$T^H = H SiO_{3/2}$;
$T^{PE} = (-CH_2 CH(R^{14})(R^{15})_t O(R^{16})_u (C_2H_4O)_v (C_3H_6O)_w (C_4H_8O)_x R^{17}) SiO_{3/2}$;
$T^E = R^E SiO_{3/2}$; and
$Q = SiO_{4/2}$;

where $R^9$, $R^{10}$, $R^{11}$, $R^{12}$, $R^{13}$, $R^{18}$, $R^{19}$, $R^{20}$, and $R^{21}$ are each independently selected from the group of monovalent hydrocarbon radicals having from 1 to 60 carbon atoms;

$R^{14}$ is H or a 1 to 6 carbon atom alkyl group; $R^{15}$ is a divalent alkyl radical of 1 to 6 carbons; $R^{16}$ is selected from the group of divalent radicals consisting of —$C_2H_4O$—, —$C_3H_6O$—, and —$C_4H_8O$—; $R^{17}$ is H, a monofunctional hydrocarbon radical of 1 to 6 carbons, or acetyl;

$R^E$ is independently a monovalent hydrocarbon radical containing one or more oxirane or oxetane moieties having from one to sixty carbon atoms;

the subscript f may be zero or positive subject to the limitation that when the subscript f is zero, h must be positive;

the subscript h may be zero or positive subject to the limitations that when h is zero, the subscript f must be positive, and that the sum of the subscripts h, l and p is positive;

the subscript k is zero or positive and has a value ranging from about 0 to about 1,000;

the subscript l is zero or positive and has a value ranging from about 0 to about 400 subject to the limitation that the sum of the subscripts h, l and p is positive;

the subscript o is zero or positive and has a value ranging from 0 to about 50;

the subscript p is zero or positive and has a value ranging from 0 to about 30 subject to the limitation that the sum of the subscripts h, l and p is positive;

the subscript s is zero or positive and has a value ranging from 0 to about 20;

the subscript i is zero or positive and has a value ranging from 0 to about 20;

the subscript m is zero or positive and has a value ranging from 0 to about 200;

the subscript q is zero or positive and has a value ranging from 0 to about 30;

the subscript j is zero or positive and has a value ranging from 0 to about 2;

the subscript n is zero or positive and has a value ranging from 0 to about 20;

the subscript r is zero or positive and has a value ranging from 0 to about 30;

the subscript t is zero or one;

the subscript u is zero or one;

the subscript v is zero or positive and has a value ranging from 0 to about 100 subject to the limitation that (v+w+x)>0;

the subscript w is zero or positive and has a value ranging from 0 to about 100 subject to the limitation that (v+w+x)>0;

the subscript x is zero or positive and has a value ranging from 0 to about 100 subject to the limitation that (v+w+x)>0;

or alternatively where the oxirane or oxetane compound is a hydrocarbon having the formula:

$$R^{22}{}_y (R^{23})_z (R^{24}{}_\alpha)(R^{25})_\beta$$

where $R^{22}$ and $R^{25}$ are independently a monovalent hydrocarbon radical containing one or more oxirane or oxetane moieties having from 3 to 12 carbon atoms;

$R^{23}$ and $R^{24}$ are each selected from the group consisting of H or a linear or branched monovalent hydrocarbon radical of 1 to 200 carbons;

the subscripts y, z, α, β are zero or positive ranging from zero to four subject to the limitation that (y+β)>2 or alternatively where the oxirane or oxetane compound is a polyether having the formula:

$$R^{26} O (R^{27})_\gamma (C_2 H_4 O)_\delta (C_3 H_6 O)_\epsilon (C_4 H_8 O)_\zeta R^{28}$$

where $R^{26}$ and $R^{28}$ are independently a monovalent hydrocarbon radical containing one or more oxirane or oxetane moieties having from 3 to 12 carbon atoms;

$R^{27}$ is selected from the group of divalent radicals consisting of —$C_2H_4O$—, —$C_3H_6O$—, and —$C_4H_8O$—;

the subscript γ is zero or 1;

the subscript δ is zero or positive and has a value ranging from 0 to about 100 subject to the limitation that (δ+ε>ζ)>0;

the subscript ε is zero or positive and has a value ranging from 0 to about 100 subject to the limitation that (δ+ε>ζ)>0;

the subscript is zero or positive and has a value ranging from 0 to about 100 subject to the limitation that $(\delta + \epsilon > \zeta) > 0$.

The present invention also provides for a reaction product of an epoxy compound and an amino silane further comprising the reaction product of a compound having the formula:

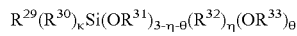

$$R^{29}(R^{30})_\kappa Si(OR^{31})_{3-\eta-\theta}(R^{32})_\eta(OR^{33})_\theta$$

where $R^{29}$ is a monovalent hydrocarbon radical containing one or more oxirane or oxetane moieties having from 3 to 12 carbon atoms;

$R^{30}$ is a divalent hydrocarbon radical consisting of 1-60 carbons and the subscript $\kappa$ has a value of zero or 1; $R^{31}$ and $R^{32}$ are independently selected from the group of monovalent linear or branched hydrocarbon radicals having from 1 to 60 carbon atoms;

the subscript $\eta$ is zero or positive and has a value ranging from 0 to 3;

the subscript $\theta$ is greater than 0 and less than or equal to 3, subject to the limitation that $3-\eta-\theta$ is greater than or equal to zero;

$R^{33}$ is a hydrocarbon radical that contains 3 to 200 carbon atoms.

As used herein the phrase hydrocarbon radical includes hydrocarbon radicals that may be optionally substituted with hetero-atoms particularly nitrogen, oxygen, and sulfur, and may optionally contain ring structures such as oxirane and oxetane groups.

Preferred Embodiments

In reacting the oxirane or oxetane compounds with amino bearing compounds, the mole ratio of oxirane or epoxy groups to amino groups is preferably about 1 to about 4, more preferably greater than about 1.1 and less than about 3.9, and most preferably greater than about 1.2 and less than about 3.8. $R^1$ is preferably a monovalent hydrocarbon radical of from 1 to about 10 carbon atoms or hydrogen, more preferably from 1 to about 5 carbon atoms or hydrogen, most preferably $R^1$ is H. $R^2$ is preferably a monovalent hydrocarbon radical of from 1 to about 10 carbon atoms more preferably 2 to about 8 carbon atoms, and most preferably 3 to about 5 carbon atoms. $R^4$ is preferably a monovalent hydrocarbon radical of from 3 to about 10 carbon atoms more preferable 3 to about 8 carbon atoms most preferable 3 to about 5 carbon atoms. $R^3$, $R^6$, $R^7$, and $R^8$ are each preferably a monovalent hydrocarbon radical of from 1 to about 20 carbon atoms more preferably 1 to about 15 carbon atoms, most preferably 2 to about 8 carbon atoms. Subscript a is in the range of from 0 to about 3, preferably from about 1 to about 3, more preferably from about 2 to about 3, most preferably from 0 to about 1. Subscript b is in the range of 0 to about 25, more preferably 0 to about 15 and most preferably 3. Subscript c is in the range 0 to about 3, more preferably 0 to about 2, most preferably 0 to about 1. $R^9$, $R^{10}$, $R^{11}$, $R^{12}$, $R^{13}$, $R^{18}$, $R^{19}$, $R^{20}$, and $R^{21}$ are each preferably a monovalent hydrocarbon radical of from 1 to about 4 carbon atoms, more preferably 1 to about 3 carbon atoms, and most preferably 1 carbon atom. The subscripts f, l, m, n, o p, q, r, s are each in the range of 0 to about 200, more preferably 0 to about 100, and most preferably 0 to about 50. The subscript k is in the range of 0 to about 500, more preferably 5 to about 250, and most preferably 5 to about 150. The subscripts v, w, and x are each in the range of 0 to about 50, more preferably 0 to about 35, and most preferably 0 to about 25. $R^{23}$ and $R^{24}$ are each preferably a monovalent hydrocarbon radical of from 5 to about 1000 carbon atoms, more preferably 10 to about 500, and most preferably 10 to about 300. The subscripts $\delta, \epsilon, \zeta$ are in the range of 0 to about 50 more preferably, 0 to about 30, and most preferably 0 to about 15. $R^{31}$ and $R^{32}$ are each preferably a monovalent hydrocarbon radical of from 1 to about 10 carbon atoms, more preferably 1 to about 8 carbon atoms, and most preferably 1 to about 4 carbon atoms. $R^{33}$ are each preferably a monovalent hydrocarbon radical of from 3 to about 100 carbon atoms, more preferably 3 to about 50 carbon atoms, most preferably 3 to about 10 carbon atoms.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Optionally the reaction of component A with component B can be conducted in the presence of a primary or secondary amine that may or may not possess a reactive alkoxy silane moiety. The result will be a reaction product of A, B, and the primary or secondary amine. Examples of these primary amines are; methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2, 3,3,4,4,5,5,6,6,7,7,8,8,8-pentadecafluoro-1-octanamine and the like. Examples of secondary amines are; methylethylamine, methylhexylamine, methyloctadecylamine, diethanolamine, dibenzylamine, dihexylamine dicyclohexylamine, piperidine, pyrrolidine phthalimide, and the like. Polymeric amines may also be used such.

Applications for Embodiments of the Invention

The product of the reaction of A, an oxirane or oxetane compound possessing two or more oxirane or oxetane groups per molecule and B, an aminosilane, results in a polymer that contains alkoxy silane functional moieties covalently bond to the polymer chain. These alkoxy silane groups may be activated particularly by hydrolysis and undergo further reactions leading to a cross-linked network. The cross-linking mechanism of silanes is usually a two-step process. The first step usually involves the hydrolysis of an alkoxy silane to form silanols. The second step usually involves the condensation of the silanol groups so produced with themselves or with other reactive organic groups. The reaction between two silanol groups leads to a thermally stable siloxane bond. Silanol groups may also condense reversibly with organic moieties such as alcohols, carboxylic acids, amines, mercaptans, and ketones (other reactive groups). The bonds that are formed are less stable than the siloxane bonds. However when a cross-linked network is formed the rate of the reverse reaction may be severely reduced or even stopped.

The compositions of the present invention may be utilized as pure components, mixtures, or emulsions. As is generally known, emulsions comprise at least two immiscible phases one of which is continuous and the other which is discontinuous. Further emulsions may be liquids or gases with varying viscosities or solids. Additionally the particle size of the emulsions may render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the composition of the present invention;
2) aqueous emulsions where the discontinuous phase comprises the composition of the present invention and the continuous phase comprises water;
3) non-aqueous emulsions where the discontinuous phase comprises a non-aqueous hydroxylic solvent and the continuous phase comprises the composition of the present invention; and
4) non-aqueous emulsions where the continuous phase comprises a non-aqueous hydroxylic organic solvent and the discontinuous phase comprises the composition of the present invention.

Depending on the choice of component A and component B it is possible to alter the hydrophilic or lipophilic properties of the resulting reaction product. Thus depending on the hydrophilic lipophilic balance, the resulting reaction product may be soluble in polar aqueous or hydroxylic solvents or it may be soluble in non-polar solvents such as oils, low molecular weight siloxanes and silicones and the like.

The hydrophilic lipophilic balance of the resulting reaction product will result in imparting different properties to articles of manufacture depending on the hydrophilic lipophilic balance of the reaction product. For example, a more hydrophilic reaction product may impart hydrophilic properties to one or more surfaces of an article of manufacture such as a textile or fibers such as hair. Conversely, a more hydrophobic reaction product may impart hydrophobic properties of one or more surfaces of an article of manufacture such as a textile or fibers such as hair. These hydrophilic or hydrophobic properties are readily measured by standardized tests. As used herein, the word textile encompasses both woven textiles and non-woven textiles made from both natural and man-made fibers. Thus treatment of woven and non-woven textiles with the reaction product of the present invention produces an enhanced response to water of the treated textile either increasing the hydrophilicity or hydrophobicity of the textile so treated as measured by standardized tests. Similarly, use of the compositions of the present invention to treat human produces an enhanced response of the skin so treated to water as measured by tests tomeasure the hydrophobic or hydrophilic properties of human skin so treated.

Hair Treatment

Hydrophobic

Upon application and curing a reaction product of the present invention to a hair tress, the resulting treated material exhibits a water contact angle of greater than 80°, more preferably greater than 85°, and most preferably greater than 90° when the contact angle technique as described in U.S. Pat. No. 6,846,333 B2 at column 4 lines 16 through 24 is performed.

Upon application and curing a reaction product of the present invention to a hair tress, the resulting treated material exhibits a strike through time of greater than 100 seconds, more preferably greater than 200 seconds, and most preferably greater than 300 seconds when AATCC Test Method 79-1992 adapted for hair is performed.

Skin Treatment

Hydrophobic

Upon application and curing a reaction product of the present invention to human skin, the resulting treated human skin exhibits a water contact angle of greater than 60° and most preferably greater than 65° when ASTM D5725-99 is performed.

Hydrophilic

Upon application and curing a reaction product of the present invention to human skin, the resulting treated human skin exhibits a water contact angle of less than 40° and most preferably less than 35° when ASTM D5725-99 is performed.

A. Personal Care

In a preferred embodiment, the epoxy amino silane copolymers of the present invention comprises, per 100 parts by weight ("pbw") of the personal care composition, from 0.01 to 99 pbw, more preferably from 0.5 pbw to 30 pbw and still more preferably from 1 to 15 pbw of the composition of the present invention and from 0.01 pbw to 99.9 pbw, more preferably from 70 pbw to 99.5 pbw, and still more preferably from 85 pbw to 99 pbw of the personal care composition.

The compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and, when sufficiently small, microemulsions may be transparent. Further it is also possible to prepare emulsions of emulsions and these are generally known as multiple emulsions. These emulsions may be:

a) aqueous emulsions where the discontinuous phase comprises water and the continuous phase comprises the epoxy amino silane copolymers of the present invention;

b) aqueous emulsions where the discontinuous phase comprises the epoxy amino silane copolymers of the present invention and the continuous phase comprises water;

c) non-aqueous emulsions where the discontinuous phase comprises a non-aqueous hydroxylic solvent and the continuous phase comprises the epoxy amino silane copolymers of the present invention; and d) non-aqueous emulsions where the continuous phase comprises a non-aqueous hydroxylic organic solvent and the discontinuous phase comprises the epoxy amino silane copolymers of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the epoxy amino silane copolymers of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the compositions of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the epoxy amino silane copolymers of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the compositions of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the compositions of the present invention, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046, 156; 6,054,547; 6,075,111; 6,077,923; 6,083,901; and 6,153, 578; all of which are herein and herewith specifically incorporated by reference.

By using compositions of the invention, we have found a simple method to provide durable films to hair or skin. This method comprises:

i) dispersing the polymer in an aqueous polar phase, preferably microemulsifying the polymer in this aqueous phase with surfactant. The surfactant may comprise a nonionic surfactant, a cationic surfactant, an anionic surfactant, an anionic surfactant, an amphoteric surfactant, or a mixture of such surfactants.

ii) Applying the aqueous dispersion or diluted microemulsion to hair or skin, in the form of sprays, creams, mousse, O/W emulsion, W/O emulsion, rinse-off products.

iii) Drying of the hair or skin in the open air at room temperature or by means involving heat.

In particular, we found that these treatments allow restoring the hydrophobicity of damaged hair, while leaving a pleasant feel and conditioning effect. This hydrophobicity is durable over the washes and helps improve the performance of conditioner for damaged hair. It also provides a remarkable thermal protection during ironing of damped hair, helping to improve the straightening of hair, which are frizzy, such as damaged colored hair, or ethnic relaxed hair. The treatment of this invention can also impart a styling benefit to aid in setting the hair in a desirable position. The compositions for hair and skin treatments comprise the above-mentioned polymer as an ingredient. They may also comprise other ingredients, which are commonly used in cosmetics such as surfactants, humectants, ultraviolet protectors, pH adjustors, preservatives, fragrance, antioxidants, chelating agents, thickening agents, film-forming ingredients, oily components, polymers or propellants provided they do not impede the effects described in this invention. As used herein personal care compositions suitable for treating hair include but are not limited to shampoos, conditioners, mousses, styling gels, permanent wave fixatives, spray, paste, moisturizing lotions and creams, combing creams, relaxers, hair dyeing products such as developers and the like.

The uses of the compositions of the present invention are not restricted to personal care compositions, other products such as waxes, polishes and textiles treated with the compositions of the present invention are also contemplated.

B. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

C. Oil and Gas

Compositions of the present organomodified silylated surfactant invention are useful in oil and gas applications, including demulsification.

D. Water Processing

Compositions comprising organomodified silylated surfactant invention are useful for applications involving commercial and industrial open recirculating cooling water towers, closed cooling water systems, cooling water conduits, heat exchangers, condensers, once-through cooling systems, Pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

Pulp and Paper

Compositions of the present organomodified silylated surfactant invention are useful in pulp and paper applications, such as paperboard defoamers, and wetting agents for the pulping process.

EXPERIMENTAL

Synthetic Examples

Personal Care Examples

Synthesis Examples

Synthesis of Polymer A

Aminopropyltriisopropoxy silane (40.77 g), an epoxy encapped polysiloxane with the average structure $CH_2(O)CHCH_2OCH_2CH_2CH_2Si(CH_3)_2O[Si(CH_3)_2O]_{50}Si(CH_3)_2CH_2CH_2CH_2OCH_2CH(O)CH_2$ (171.40 g) and an epoxy endcapped polyether with the average structure $CH_2(O)CHCH_2O(CH_2(CH_3)CH_2O)_7CH_2CH(O)CH_2$ (37.83 g) and isopropanol (425.68 g) was combined in a 500 mL flask. The material was brought to reflux and stirred with an overhead stirrer. The refluxing continued for 15.5 hr until all epoxy groups were consumed as determined by titration. The material was transferred to a rotary evaporator and stripped at 70° C. and 4 torr for 2 hrs to remove the isopropanol.

Synthesis of Polymer B

Aminopropyltriisopropoxy silane (41.45 g), 3-(diethylamino)propylamine (20.49 g), an epoxy encapped polysiloxane with the average structure $CH_2(O)CHCH_2OCH_2CH_2CH_2Si(CH_3)_2O[Si(CH_3)_2O]_{50}Si(CH_3)_2CH_2CH_2CH_2OCH_2CH(O)CH_2$ (348.56 g) and an epoxy encapped polyether with the average structure $CH_2(O)CHCH_2O(CH_2(CH_3)CH_2O)_7CH_2CH(O)CH_2$ (89.49 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer C

Aminopropyltriisopropoxy silane (16.78 g), 3-(diethylamino)propylamine (24.88 g), an epoxy encapped polysiloxane with the average structure $CH_2(O)CHCH_2OCH_2CH_2CH_2Si(CH_3)_2O[Si(CH_3)_2O]_{50}Si(CH_3)_2CH_2CH_2CH_2OCH_2CH(O)CH_2$ (344.45 g) and an epoxy encapped polyether with the average structure $CH_2(O)CHCH_2O(CH_2CH_2O)_{14}CH_2CH(O)CH_2$ (88.44 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer D

Aminopropyltriisopropoxy silane (11.71 g), 3-(diethylamino)propylamine (5.79 g), an epoxy encapped polysiloxane with the average structure $CH_2(O)$ $CHCH_2OCH_2CH_2CH_2Si(CH_3)_2O[Si(CH_3)_2O]_{250}Si(CH_3)_2$ $CH_2CH_2CH_2O\ CH_2CH(O)CH_2$ (457.22 g) and an epoxy encapped polyether with the average structure $CH_2(O)$ $CHCH_2O(CH_2CH_2O)_{14}CH_2CH(O)CH_2$ (25.28 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer E

Aminopropyltriisopropoxy silane (22.68 g), an epoxy encapped polysiloxane with the average structure $CH_2(O)$ $CHCH_2OCH_2CH_2CH_2Si(CH_3)_2O[Si(CH_3)_2O]_{30}Si(CH_3)_2$ $CH_2CH_2CH_2OC\ H_2CH(O)CH_2$ (227.34 g) and isopropanol (50 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer F

Aminopropyltriisopropoxy silane (15.91 g), an epoxy encapped polysiloxane with the average structure $CH_2(O)$ $CHCH_2OCH_2CH_2CH_2Si(CH_3)_2O[Si(CH_3)_{50}]Si(CH_3)_2$ $CH_2CH_2CH_2OC\ H_2CH(O)CH_2$ (66.91 g) and an epoxy encapped polyether with the average structure $CH_2(O)$ $CHCH_2O(CH_2CH_2O)_{14}CH_2CH(O)CH_2$ (17.18 g) and isopropanol (50 g) was combined in a 500 mL flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol.

Synthesis of polymer G Aminopropyltriisopropoxy silane (49.44 g), an epoxy encapped polysiloxane with the average structure $CH_2(O)CHCH_2OCH_2CH_2CH_2Si(CH_3)_2O[Si(CH_3)_2O]_{100}Si(CH_3)_2CH_2CH_2CH_2O\ CH_2CH(O)CH_2$ (397.22 g) and an epoxy encapped polyether with the average structure $CH_2(O)CHCH_2O(CH_2CH_2O)_{14}CH_2CH(O)CH_2$ (53.33 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer H

Aminopropyltriisopropoxy silane (25.35 g), 3-(diethylamino)propylamine (12.53 g), an epoxy encapped polysiloxane with the average structure $CH_2(O)$ $CHCH_2OCH_2CH_2CH_2Si(CH_3)_2[Si(CH_3)_2O]_{100}Si(CH_3)_2$ $CH_2CH_2CH_2O\ CH_2CH(O)CH_2$ (407.38 g) and an epoxy encapped polyether with the average structure $CH_2(O)$ $CHCH_2O(CH_2CH_2O)_{14}CH_2CH(O)CH_2$ (54.74 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer I

Aminopropyltriisopropoxy silane (18.26 g), 3-(diethylamino)propylamine (9.03 g), an epoxy encapped polysiloxane with the average structure $CH_2(O)$ $CHCH_2OCH_2CH_2CH_2Si(CH_3)_2O[Si(CH_3)_2O]_{150}Si(CH_3)_2$ $CH_2CH_2CH_2O\ CH_2CH(O)CH_2$ (433.298 g) and an epoxy encapped polyether with the average structure $CH_2(O)$ $CHCH_2O(CH_2CH_2O)_{14}CH_2CH(O)CH_2$ (39.42 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer J

Aminopropyltriisopropoxy silane (14.27 g), 3-(diethylamino)propylamine (7.05 g), an epoxy encapped polysiloxane with the average structure $CH_2(O)$ $CHCH_2OCH_2CH_2CH_2Si(CH_3)_2O[Si(CH_3)_2O]_{200}Si(CH_3)_2$ $CH_2CH_2CH_2O\ CH_2CH(O)CH_2$ (447.87 g) and an epoxy encapped polyether with the average structure $CH_2(O)$ $CHCH_2O(CH_2CH_2O)_{14}CH_2CH(O)CH_2$ (30.81 g) and isopropanol (500 g) was combined in a 2000 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Synthesis of Polymer K

An epoxy encapped polyether (148.28 g) with the average structure of $CH_2(O)CHCH_2O(CH_2CH_2O)_{22}CH_2CH(O)CH_2$, aminopropyltriisopropoxysilane (51.72 g) and isopropanol (60.00 g) were combined in a 500 mL round bottom flask. The solution was heat to reflux and stirred with a magnetic stirrer. The reaction was allowed to remain at reflux until all the epoxy groups were consumed as determined by titration. The resulting material exhibited a dark straw color. The material was transferred to a rotary evaporator and stripped at 70° C. and 4 torr for 2 hrs to remove the isopropanol.

Synthesis of Polymer L

Aminopropyltriisopropoxy silane (7.57 g), an epoxy encapped polysiloxane with the average structure $CH_2(O)$ $CHCH_2OCH_2CH_2CH_2Si(CH_3)_2O[Si(CH_3)_2O]_{399}Si(CH_3)_2$ $CH_2CH_2CH_2O\ CH_2CH(O)CH_2$ (234.25 g) and an epoxy encapped polyether with the average structure $CH_2(O)$ $CHCH_2O(CH_2CH_2O)_{14}CH_2CH(O)CH_2$ (8.18 g) and isopropanol (250 g) was combined in a 1000 mL flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol.

Examples of Copolymer Containing Emulsions

Emulsion A1, F1, L1, K1 and C2 are prepared by mixing the polymer and water with a lab propeller mixer for 15 min. The dispersions are then acidified and homogenized for 1 minute.

100 g of the microemulsions B1-E1, A2 and G1-J1 are prepared by method (i)

Method (i)

The polymer is mixed with the surfactant system and 10 g of water to obtain an homogeneous mixture, using a regular lab propeller mixer or a speed mixer. The remaining water is added slowly. The acidification is performed at the end. Clear microemulsions should be obtained.

100 g of microemulsion F2 are prepared by method (ii)
Method (ii)

The polymer and the surfactant are mixed with 0.6 g water to form a gel-like mixture and added to the acidified water, while stirring. The emulsions presented in Table 1 will be used as master emulsions to prepare the dilute hair treatments described in the following sections.

Hydrophobizing Hair Treatments

Samples of copolymer containing emulsions presented in Table 1 were diluted in water to obtain dispersions containing 0.3% and 1% weight percent copolymers. Double-bleached tresses purchased from Hair International Importer and Products were used as sample of damaged hair to test the copolymer containing treatments. Each tress weighs about 4 g. Each tress was dipped into 100 ml of the dilute dispersion for 60 s and blown dry. The tress was then shampooed with a 10% SLES solution then rinsed.

The hydrophobicity was measured on untreated and treated hair either by determining the contact angle between distilled water and the surface of single hair fibers using a microbalance (Thermocahn). Description of the technique has been described for example in U.S. Pat. No. 6,846,333 B2.

The measurement consists of measuring the force exerted by the water on the hair fiber during its immersion in the distilled water (advancing contact angle). The force measured is related to the contact angle between the water and the surface of the hair by the relationship: $F=P*g*\cos q$ where F is the force expressed in Newton, P is the circumference of the hair, g is the surface tension of water, and q the contact angle. The hair is considered hydrophilic when the advancing angle ranges from 0 to less than 80 and hydrophobic when this angle ranges from 80 to 180.

For each treated tress, 5 fibers taken randomly are mounted on a very fine metallic hook. The circumference is derived from the hair fiber diameter, measured using a Mitutoyo laser scan micrometer. The value reported in the table 3 is the contact angle average of 5 hair fibers.

The hydrophobicity of the hair tress was also evaluated by measuring the time required for a drop of water to penetrate the surface of the hair tress secured horizontally on a clamp (Murakami hair tress holder) according to a method adapted from the AATCC Test Method 79-1992 for textile samples. The hair tress is held taut into the Murakami hair holder. A drop of deionized water was applied onto the tress surface via a dropper and a timer was started. The timer was stopped when the drop of water completely penetrated the tress and was record in seconds. The value reported is the average of three drop tests readings, shown in the table 3. The test was terminated at 300 seconds. A value of 300 seconds indicates that the drop never penetrated the hair tress.

The comparative experiments for those examples are the following:

TABLE 1

| Emulsion | A1 | B1 | C1 | D1 | E1 | F1 | F2 | A2 |
|---|---|---|---|---|---|---|---|---|
| polymer A | 1 | | | | | | | 20 |
| polymer B | | 20 | | | | | | |
| polymer C | | | 15 | | | | | |
| polymer D | | | | 20 | | | | |
| polymer E | | | | | 20 | | | |
| polymer F | | | | | | 20 | 9 | |
| polymer G | | | | | | | | |
| polymer H | | | | | | | | |
| polymer I | | | | | | | | |
| polymer J | | | | | | | | |
| polymer K | | | | | | | | |
| polymer L | | | | | | | | |
| TMN-6 | | 10 | 7.5 | | 10 | | 1.3 | 10 |
| TMN-3 | | | | 4.6 | | | | |
| TMN-10 | | | | 5.4 | | | | |
| Citric acid(10 wt %) | | | qs pH = 4 | | | | qs pH = 4 | |
| acetic acid | qs pH = 4 | qs pH = 4 | | qs pH = 4 | qs pH = 4 | qs pH = 4 | | qs pH = 4 |
| water | qs 100 | qs 100 | qs 100 | qs 100 | qs 100 | qs 100 | qs 100 | qs 100 |

| Emulsion | G1 | H1 | I1 | J1 | K1 | C2 | L1 |
|---|---|---|---|---|---|---|---|
| polymer A | | | | | | | |
| polymer B | | | | | | | |
| polymer C | | | | | | 50 | |
| polymer D | | | | | | | |
| polymer E | | | | | | | |
| polymer F | | | | | | | |
| polymer G | 19 | | | | | | |
| polymer H | | 20 | | | | | |
| polymer I | | | 20 | | | | |
| polymer J | | | | 20 | | | |
| polymer K | | | | | 5 | | |
| polymer L | | | | | | | 25 |
| TMN-6 | 9.2 | 10 | | | | 10 | 7 |
| TMN-3 | | | 4.6 | 4.6 | | | |
| TMN-10 | | | 5.4 | 5.4 | | | 5.5 |
| Citric acid(10 wt %) | | | | | | | |
| acetic acid | qs pH = 4 | qs pH = 4 | qs pH = 4 | qs pH = 4 | qs pH = 4 | qs pH = 4 | qs pH = 4 |
| water | qs 100 | qs 100 | qs 100 | qs 100 | qs 100 | qs 100 | qs 100 |

TABLE 2

| | |
|---|---|
| comparative 1 | virgin caucasian black hair untreated |
| comparative 2 | double-bleached hair untreated |
| comparative 3 | double-bleached hair untreated after 1 (shampoo + conditioner) cycle |
| comparative 4 | double-bleached hair treated with 400 ppm quaternized silicone |

The shampoo is a 10% sales solution and the conditioner is a silicone containing shampoo from Procter and Gamble, Pantene Pro Daily Moisture Renew. The conditioning quaternized silicone is Silsoft Q from Momentive Performance Material.

The results of the hydrophobicity tests are shown in table 3. Table 3 shows that untreated damaged hair (Comparative 2) is hydrophilic, whereas virgin untreated hair (Comparative 1) is hydrophobic. Regular conditioning silicone from rinse-off conditioner do not change the damaged hair hydrophophilicity (Comparative 3-4). In contrast, the hair treated with the polymer described in the present invention are hydrophobic (Example 1-6).

TABLE 3

Hydrophobicity data

| | copolymer concentration % | advancing contact angle | strike through time (s) | hair hydrophobicity |
|---|---|---|---|---|
| example 1 | 1% from emulsion A1 | 105 | >300 | hydrophobic |
| example 2 | 0.3% from emulsion B1 | 121 | >300 | hydrophobic |
| | 1% from emulsion B1 | 106 | >300 | hydrophobic |
| example 3 | 0.3% from emulsion C1 | 104 | >300 | hydrophobic |
| | 1% from emulsion C1 | 109 | >300 | hydrophobic |
| example 4 | 1% from emulsion D1 | 106 | >300 | hydrophobic |
| example 5 | 1% from emulsion E1 | — | >300 | hydrophobic |
| example 6 | 1% from emulsion F1 | — | >300 | hydrophobic |
| comparative 1 | | 94 | >300 | hydrophobic |
| comparative 2 | | 59 | 0 | hydrophilic |
| comparative 3 | | 78 | 0 | hydrophilic |
| comparative 4 | | 45 | 0 | hydrophilic |

Durability from Wash

In order to evaluate the durability of the hair treatments to wash cycles, the hydrophobicity was tested after 20 washes on damaged hair (double-bleached) using the contact angle method described above. These values are reported in Table 4, along with the values of contact angle after 1 wash cycle. Comparative 5 showed the values of contact angle for damaged hair washed and conditioned 1 time and 20 times with the shampoo/conditioner system described for Comparative 3. The data show that the contact angle of the hair treated with the copolymer disclosed in this invention is higher than 80 degree after 20 washes, indicating that the hydrophobizing treatment can endure 20 washes.

TABLE 4

Hydrophobicity durability determined by single fiber contact angle

| | copolymer concentration % | 1 wash advancing contact angle | 20 wash advancing contact angle |
|---|---|---|---|
| example 1 | 1% from emulsion A1 | 105 | 94 |
| example 2 | 0.3% from emulsion B1 | 121 | 81 |
| | 1% from emulsion B1 | 106 | 104 |
| example 3 | 0.3% from emulsion C1 | 104 | 120 |
| | 1% from emulsion C1 | 109 | 108 |
| example 4 | 1% from emulsion D1 | 106 | 86 |
| comparative 5 | | 78 | 63 |

Durability of the hair treatment is also displayed in Table 5 where comparative 5 is the double-bleached untreated hair subjected to 1, 10, 20 washing cycles. The treatment is considered durable after 10 washes or after 20 washes, if the strike through time is higher than 10 s.

TABLE 5

Hydrophobicity durability determined by strike through time

| | Copolymer concentration % | strike through time (s) | | |
|---|---|---|---|---|
| | | 1 wash | 10 wash | 20 wash |
| example 2 | 0.3% from emulsion B1 | 300 | 192 | 99 |
| | 1% from emulsion B1 | 300 | 300 | 300 |
| example 3 | 0.3% from emulsion C1 | 300 | 300 | 72 |
| | 1% from emulsion C1 | 300 | 132 | 68 |
| example 4 | 0.3% from emulsion D1 | 37 | 1 | 0 |
| | 1% from emulsion D1 | 300 | 39 | 21 |
| comparative 5 | | 0 | 0 | 0 |

Rinse-off Treatment

Rinse-off conditioner having the composition shown in Table 6 was prepared. Double bleached tresses were washed with 10% SLES solution and conditioned with composition in example 7 and rinsed for 30 s. Hydrophobicity tests were performed on the treated and untreated tress. Table 7 demonstrates that copolymer containing rinse-off conditioner provides hydrophobizing treatment to the hair, which are durable through 20 washes.

TABLE 6

|  | Example 7 Weight % |
|---|---|
| Glyceryl stearate (and) ceteareth-20 and ceteareth-12 and cetearyl alcohol and cetyl palmitate * | 10% |
| Copolymer from emulsion C1 | 2% |
| Water | q.s to 100% |

* trademane: Emulgade SE-PF from Cognis

TABLE 7

|  | advancing contact angle | | strike through time (s) | | |
|---|---|---|---|---|---|
|  | 1 wash | 20 wash | 1 wash | 10 wash | 20 wash |
| example 7 | 112 | 95 | 300 | 300 | 27 |
| comparative 5 | 78 | 63 | 0 | 0 | 0 |

Mousse Formulation

An aqueous mousse composition having the composition shown in Table 8 was prepared.

Double bleached tresses were washed with 10% SLES solution and dried. The composition was poured into a container equipped with a manual pump. 2 g of the mousse was applied to the 4 g tress by massaging. The tresses were dried with a blow drier. Hydrophobicity and durability tests were performed on treated and untreated tress. Table 9 demonstrates that copolymer delivered from a mousse formulation provides a hydrophobizing treatment to damaged hair which are durable through 20 washes, as shown by the strike through time data.

TABLE 8

| Mousse formulation | |
|---|---|
|  | Example 8 Weight % |
| Decyl glucoside | 0.5% |
| Copolymer from emulsion C1 | 2% |
| Water | q.s to 100% |

*Trademark: Plantaren 2000N

TABLE 9

| Hydrophobicity and durability data | | | | | |
|---|---|---|---|---|---|
|  | advancing contact angle | | strike through time (s) | | |
|  | 1 wash | 20 wash | 1 wash | 10 wash | 20 wash |
| example 8 | 105 | 79 | 300 | 190 | 20 |
| comparative 5 | 78 | 63 | 0 | 0 | 0 |

Conditioning Performance

The conditioning performance of the hair treated with copolymers disclosed in this invention were evaluated using dry combing force procedure using a Diastron combing force apparatus.

Diastron Dry Combing Test Diastron dry combing procedures are well recognized and well accepted in the industry for determining hair conditioning by the ease of dry combing. The test employs a strain gauge, which is equipped to measure the force required to comb the hair. The conditioning performance is based on the ability of a particular hair treatment formulation to reduce the force required to comb the hair.

Hair Tress Preparation.

Double bleached blond hair 4 g tresses (15 cm long) were purchased from Hair International INC. Prior to washing, each tress is dipped into 0.5% Sodium Hydroxide solution for two minutes and rinsed for two minutes with tap water. Each tress is then washed with 1 ml of a 10% SLES solution and rinsed using a standard wash protocol. After washing, the wet tresses are combed with a fine teeth comb, dried in a blow drier bonnet and kept overnight in a environmental chamber at 50% RH before combing force measurement. These clean tresses are used to measure the baseline combing force, according to the combing force protocol described below. After the baseline measurement, the control tresses (comparative) are washed again with the SLES solution and treated with a conditioner (1 ml/tress) described below. In contrast, after the baseline measurement, the test tresses were dipped into 100 ml of the dilute dispersion of copolymer containing emulsions described in Table 1 for 60 s and blown dry. After rinsing and drying and combing, the treated tresses are kept overnight in an environmental chamber at 50% RH before combing force measurement.

Dry Combing Force Measurement:

The Diastron combing force apparatus is enclosed in a controlled humidity chamber, equilibrated at 50% RH. The automated comb speed is 500 mm/min. The combing force measurement is repeated 10 times on each tress. Each treatment is duplicated.

The combing force reduction is calculated for each tress according to the formula $$\% \text{ average force reduction} = (A_o - A) \ast 100/A_o$$

where $A_o$ is the average combing load of the baseline tress and A is the average combing load of the treated tress. The higher the average force reduction is, the higher is the conditioning performance of the treatment.

The results of Diastron dry combing force are shown in Table 10. Comparative 6 is a tress washed with two successive 10% SLES shampoo. Table 10 shows that the copolymer containing hair treatment provides a significant reduction in dry combing force, that are superior to comparative 3 (commercial conditioner).

TABLE 10

| Dry combing force data | | |
|---|---|---|
|  | copolymer concentration % wt | Combing force reduction % |
| example 3 | 1% from emulsion C1 | 76 |
| example 9 | 1% from emulsion F2 | 71 |
| example 10 | 1% from emulsion A2 | 70 |
| example 11 | 1% from emulsion G1 | 81 |
| comparative 3 |  | 65 |
| comparative 6 |  | 27 |

Conditioning Boosting Effect Data

Combing force data generated according to the protocol described above are shown in Table 11. Table 11 shows that the copolymer treatment provides conditioning at lower dose (example 12). But it also helps regular conditioner to perform better on damaged hair (example 13).

TABLE 11

Dry combing force data

| | copolymer concentration % wt | post treatment | Combing force reduction % |
|---|---|---|---|
| example 12 | 0.1% from emulsion F2 | shampoo | 75 |
| example 13 | 0.1% from emulsion F2 | shampoo + conditioner | 84 |
| comparative 7 | | shampoo | 53 |
| comparative 3 | | shampoo + conditioner | 65 |

Thermal Protection

Copolymer containing treatment and comparative treatments are shown in Table 12. 15 cm long double-bleached 4 g tresses from Hair International were used. The tresses were treated with a strong base (0.5% NaOH solution) in order to induce a very visible frizziness. The tresses were then washed with a 10% SLES solution, blow-dried, disentangled with a comb and kept in a 50% RH room. The test tress was dipped in the dispersion described in Table 12 for 60s. Excess water was removed by squeezing the wet tress between the index and middle finger. The damp tress is then ironed at medium heat, in a Revlon flat iron. A visual and tactile assessment was performed after the damp ironing step. The tress A treated with tap water showed strong disarray of fibers and knotting. It looked that a large number of fibers had melted and jammed during the damp iron process. This tress felt very coarse and dry to the touch. The tress C, D and E treated with commercial silicones or leave-in commercial conditioner, showed a very similar behavior. In contrast, the hair in tress B treated with 1% copolymer from emulsion Cl looked very aligned and straight with no significant frizziness. The hair felt smooth and soft to touch. Clearly the copolymer treated tress provided significant thermal protection during damp ironing, compared to all the other treatments allowing the removal of the initial tress frizzines without severe damage and a clear perceivable hair condition improvement.

TABLE 12

Hair treatment for damp iron

| Tress | | |
|---|---|---|
| A | Comparative 8 | Damp iron with tap water |
| B | Example 14 | Damp iron with 1% copolymer from emulsion C1 |
| C | Comparative 9 | Damp iron with 1% aminosilicone |
| D | Comparative 10 | Damp iron with 1% quaternized silicone |
| E | Comparative 11 | Damp iron with leave-in conditioner |

Aminosilicone and quaternized silicone in comparative 9 and 10 are from the emulsion Silsoft SME253 and Silsoft Q from Momentive Performance Materials. The leave-in conditioner is the leave-in strengthener from SoftShee Carson Optimum Care relaxing kit.

Damage Repair Experiment

Frizziness Removal Test

As in the previous experiment, 15 cm long double-bleached 4 g tresses from Hair International, held by a polymer bar at the root end were used. The hair frizziness induced by the harsh base treatment described earlier manifests itself by a significant increase of the tress volume. The volume increase of the tress was evaluated by measuring with a ruler the maximum width Lt of the tress in the hair tip region and the width of the tress at the root end Lr(polymer bar width). A volume factor was defined by the ratio Lt/Lr. The hair tress was considered very straight and not frizzy if Lt/Lr is less or equal to 2.6, as shown by the virgin untreated straight tress (comparative 12). Volume ratio much higher than 3 indicated very high level of frizziness and high damage. The volume factor measured before and after ironing, for each treatment is displayed in Table 13. The experiment was performed in duplicate. The data showed that the copolymer treatment during ironing allowed a significant removal of frizziness, superior to the aminosilicone treatment. It was also noticed that the copolymer treated tress felt very smooth, without heaviness. Similar results were observed with relaxed ethnic hair.

TABLE 13

| | Copolymer concentration % | volume factor | |
|---|---|---|---|
| | | before iron | after iron |
| example 15 | 3% from emulsion C1 | 4.5 | 2.3 |
| example 16 | 3% from emulsion D1 | 4.4 | 2.6 |
| example 17 | 3% from emulsion F2 | 4.3 | 2.6 |
| comparative 8 | | 4.3 | hair melted |
| comparative 12 | | 2.3 | 2.3 |
| comparative 13 | 3% aminosilicone | 4.8 | 3.5 |

Comparative 12 is the virgin untreated straight hair. The aminosilicone in comparative 13 is prepared with Silsoft SME253 from Momentive Performance Materials.

Styling Experiment

Virgin European brown hair was employed for this experiment. The tresses were treated with a 0.5% emulsions of copolymers polymer K and polymer C and wrapped around 1" curlers. The hair was dried in an oven at 100° C. for 1 hour then placed in 25° C. at 50% relative humidity chamber overnight to condition. The hair was removed from the roller and hung vertically in a 25° C. and 90% relative humidity chamber. The hold of the treatment was determined by the length of the tress and by the width. As the hair uncoiled and straightened, the overall length of the tress would increase. Also, as volume increase due to lack of hold, the width increased as well. Shown in the table 14 are the results. The treatments do provide a styling benefit to the hair, manifested by a reduced width of the curl upon exposure to moisture. Although the hair is not held as tight as the commercial formulation, the hair remains soft and pleasant to touch. The reduced width increase indicates a reduction in "fly away" and frizzyness of the hair. The commercial formulation is hard and does not exhibit desirable sensory.

TABLE 14

Curl retention data

| | Hair Tress Length (cm) | | | Maximum Hair Tress Width (cm) | |
|---|---|---|---|---|---|
| Treatment | Initial | 15 min | 30 min | Initial | 2 hr |
| Water | 7.7 | 12.8 | 13.5 | 2.2 | 4.3 |
| SME253 | 9.0 | 12.8 | 13.5 | 2.2 | 4.2 |
| polymer C | 8.3 | 12.2 | 13.5 | 2.3 | 2.0 |
| Studio | 3.8 | 5.1 | 5.8 | 1.7 | 2.3 |
| polymer K | 7.7 | 10.9 | 12.2 | 1.7 | 2.0 |

Contact Angle on Skin

Leg skin cut from *Sus scrofa* (pig) was used for evaluation of the effect of this invention on the surface properties of skin. A strip of skin measureing 1 cm×3 cm was cut. 0.3 g of the emulsions (C1, E1, and were coated over the skin using a pipet to level the material. The coating was allowed to dry under ambient conditions for 2 hours. The surface hydropholicity or hydrophobicity was measured using a goniometer. The contact angle of pure water was measured at 1 second after the drop was placed on the surface. A total of 50 measurements were performed on each sample. The results are shown in the table below. The product of this invention increased hydrophobicity when emulsion C1 was applied and increase hydrophiliciy when emulsion K1 was applied.

|  | Untreated | Emulsion E1 | Emulsion C1 | Emulsion K1 |
|---|---|---|---|---|
| Average | 60.7° | 44.6° | 68.5° | 4.0° |

Removability from Skin

In order to examine the adhesion characteristics to skin leg skin cut from *Sus scrofa* (pig) was used. Two emulsions were tested C2 and L1. The emulsions (1 g) was applied to the surface of a piece of skin (1 cm×3 cm) and allowed to dry overnight. The film that resulted from emulsion C2 was tacky and very difficult to remove from the skin. The film resulting from L1 was easy to remove and no residue remained on the skin after gently peeling the coating away.

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. Such ranges may be viewed as a Markush group or a collection of Markush groups consisting of differing pairwise numerical limitations which group or groups is or are fully delimited by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

The invention claimed is:

1. A personal care composition suitable for treating hair comprising a composition comprising the reaction product of
    a) oxirane or oxetane compound comprising at least two oxirane or oxetane groups; and
    b) an amino silane having the formula:

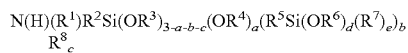

with $R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscripts a is zero or a positive number less than or equal to 3, the subscripts b and c are zero or positive and have a value ranging from 0 to 3 subject to the limitation that (a+b+c)≤3;
the subscripts d and e are zero or positive and have a value ranging from 0 to 3 subject to the limitation that (d+e)=3, wherein when hair is treated with said personal care composition said hair has a hydrophobic response to water or wherein when human skin is treated with said personal care composition said skin exhibits an enhanced hydrophobic response to water,
wherein the oxirane or oxetane compound is a siloxane having the formula:

wherein
$M^E = R^{12}R^{13}(R^E)SiO_{1/2}$
$D = R^{18}R^{19}SiO_{2/2}$
where $R^{12}$, $R^{13}$, $R^{18}$, and $R^{19}$ are methyl groups,
$R^E$ is —(CH$_2$)$_3$OCH$_2$CH(O)CH$_2$
subscript h is 2 and subscript k is 50.

2. The reaction product of claim 1 further comprising the reaction product of a compound having the formula:

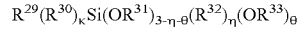

where $R^{29}$ is a monovalent hydrocarbon radical containing one or more oxirane or oxetane moieties having from 3 to 12 carbon atoms;
$R^{30}$ is a divalent hydrocarbon radical consisting of 1-60 carbons and the subscript κ has a value of zero or 1; $R^{31}$ and $R^{32}$ are independently selected from the group of monovalent linear or branched hydrocarbon radicals having from 1 to 60 carbon atoms;
the subscript η is zero or positive and has a value ranging from 0 to 3;
the subscript θ is greater than 0 and less than or equal to 3, subject to the limitation that 3-η-θ is greater than or equal to zero;
$R^{33}$ is a hydrocarbon radical that contains 3 to 200 carbon atoms.

3. The reaction product of claim 1 wherein
$R^1$ has from one to ten carbon atoms;
$R^2$ has from one to ten carbon atoms;
$R^4$ has from three to ten carbon atoms;
$R^3$, $R^6$, $R^7$, and $R^8$ each independently have from one to twenty carbon atoms.

4. The reaction product of claim 1 wherein
$R^1$ has from one to five carbon atoms;
$R^2$ has from two to eight carbon atoms;
$R^4$ has from three to eight carbon atoms;
$R^3$, $R^6$, $R^7$, and $R^8$ each independently have from one to fifteen carbon atoms.

5. The reaction product of claim 1 wherein
$R^1$ is hydrogen;
$R^2$ has from two to five carbon atoms;
$R^4$ has from three to five carbon atoms;
$R^3$, $R^6$, $R^7$, and $R^8$ each independently have from two to eight carbon atoms.

6. The reaction product of claim 2 wherein
$R^1$ has from one to ten carbon atoms;
$R^2$ has from one to ten carbon atoms;
$R^4$ has from three to ten carbon atoms;
$R^3$, $R^6$, $R^7$, and $R^8$ each independently have from one to twenty carbon atoms.

7. An aqueous emulsion where the discontinuous phase comprises water and the emulsion comprises the composition of claim 1.

8. An aqueous emulsion where the discontinuous phase comprises water and the emulsion comprises the composition of claim 2.

9. An aqueous emulsion where the discontinuous phase comprises water and the emulsion comprises the composition of claim 3.

10. An aqueous emulsion where the discontinuous phase comprises water and the emulsion comprises the composition of claim 4.

11. An aqueous emulsion where the discontinuous phase comprises water and the emulsion comprises the composition of claim 5.

12. An aqueous emulsion where the discontinuous phase comprises water and the emulsion comprises the composition of claim 6.

13. An aqueous emulsion where the continuous phase comprises water and the emulsion comprises the composition of claim 1.

14. An aqueous emulsion where the continuous phase comprises water and the emulsion comprises the composition of claim 2.

15. An aqueous emulsion where the continuous phase comprises water and the emulsion comprises the composition of claim 3.

16. An aqueous emulsion where the continuous phase comprises water and the emulsion comprises the composition of claim 4.

17. An aqueous emulsion where the continuous phase comprises water and the emulsion comprises the composition of claim 5.

18. An aqueous emulsion where the continuous phase comprises water and the emulsion comprises the composition of claim 6.

19. An non-aqueous emulsion where the discontinuous phase comprises a non-aqueous hydroxylic solvent and the emulsion comprises the composition of claim 1.

20. An non-aqueous emulsion where the discontinuous phase comprises a non-aqueous hydroxylic organic solvent and the emulsion comprises the composition of claim 2.

21. An non-aqueous emulsion where the discontinuous phase comprises a non-aqueous hydroxylic organic solvent and the emulsion comprises the composition of claim 3.

22. An non-aqueous emulsion where the discontinuous phase comprises a non-aqueous hydroxylic organic solvent and the emulsion comprises the composition of claim 4.

23. An non-aqueous emulsion where the discontinuous phase comprises a non-aqueous hydroxylic organic solvent and the emulsion comprises the composition of claim 5.

24. An non-aqueous emulsion where the discontinuous phase comprises a non-aqueous hydroxylic organic solvent and the emulsion comprises the composition of claim 6.

25. A non-aqueous emulsion where the continuous phase comprises a non-aqueous hydroxylic organic solvent and the emulsion comprises the composition of claim 1.

26. An non-aqueous emulsion where the continuous phase comprises a non-aqueous hydroxylic organic solvent and the emulsion comprises the composition of claim 2.

27. An non-aqueous emulsion where the continuous phase comprises a non-aqueous hydroxylic organic solvent and the emulsion comprises the composition of claim 3.

28. An non-aqueous emulsion where the continuous phase comprises a non-aqueous hydroxylic organic solvent and the emulsion comprises the composition of claim 4.

29. An non-aqueous emulsion where the continuous phase comprises a non-aqueous hydroxylic organic solvent and the emulsion comprises the composition of claim 5.

30. An non-aqueous emulsion where the continuous phase comprises a non-aqueous hydroxylic organic solvent and the emulsion comprises the composition of claim 6.

31. A method for treating hair comprising contacting hair with the composition of claim 1.

32. The method for treating hair of claim 31 wherein the composition is an emulsion composition comprising a continuous phase which comprises the reaction product of (a) and (b), and a discontinuous phase which comprises water or a non-aqueous hydroxylic solvent.

33. The method for treating hair of claim 31 wherein the composition is an emulsion composition comprising a discontinuous phase which comprises the reaction product of (a) and (b), and a continuous phase which comprises water or a non-aqueous hydroxylic solvent.

34. A method for treating damaged hair comprising contacting damaged hair with a composition comprising the reaction product of
a) an oxirane or oxetane compound comprising at least two oxirane or oxetane groups; and
b) an amino silane having the formula:

$$N(H)(R^1)R^2Si(OR^3)_{3-a-b-c}(OR^4)_a(R^5Si(OR^6)_d(R^7)_e)_b R^8_c$$

with $R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscripts a is zero or a positive number less than or equal to 3, the subscripts b and c are zero or positive and have a value ranging from 0 to 3 subject to the limitation that (a+b+c)<3; and
the subscripts d and e are zero or positive and have a value ranging from 0 to 3 subject to the limitation that (d+e)=3,
wherein the oxirane or oxetane compound is a siloxane having the formula:

$$M^E_h D_k$$

wherein
$M^{E=R^{12}}R^{13}(R^E)SiO_{1/2}$
$D=R^{18}R^{19}SiO_{2/2}$ where $R^{12}$, $R^{13}$, $R^{18}$, and $R^{19}$ are methyl groups,
$R^E$ is —$(CH_2)_3OCH_2CH(O)CH_2$
subscript h is 2 and subscript k is 50.

35. The method of treating damaged hair of claim 34 wherein the composition is an emulsion composition comprising a continuous phase which comprises the reaction product of (a) and (b), and a discontinuous phase which comprises water or a non-aqueous hydroxylic solvent.

36. The method of treating damaged hair of claim 34 wherein the composition is an emulsion composition comprising a discontinuous phase which comprises the reaction product of (a) and (b), and a continuous phase which comprises water or a non-aqueous hydroxylic solvent.

37. A method for treating thermally damaged hair comprising contacting thermally damaged hair with a composition comprising the reaction product of
   a) an oxirane or oxetane compound comprising at least two oxirane or oxetane groups; and
   b) an amino silane having the formula:

$$N(H)(R^1)R^2Si(OR^3)_{3-a-b-c}(OR^4)_a(R^5Si(OR^6)_d(R^7)_e)_b R^8{}_c$$

with $R^1$ is chosen from the group consisting of H or a monovalent hydrocarbon radical containing one to 20 carbon atoms;
   $R^2$ is selected from a group consisting of a divalent linear or branched hydrocarbon radical consisting of 1-60 carbons;
   $R^4$ is a hydrocarbon radical that contains 3 to 200 carbon atoms;
   $R^5$ is selected from a group consisting of oxygen or a divalent linear or branched hydrocarbon radical consisting of 1-60 carbons;
   $R^3$, $R^6$, $R^7$, and $R^8$ and are each independently selected from the group of monovalent linear or branched hydrocarbon radicals having from 1 to 200 carbon atoms;

the subscripts a is zero or number less than or equal to 3, the subscripts b and c are zero or positive and have a value ranging from 0 to 3 subject to the limitation that (a+b+c)≤3; and the subscripts d and e are zero or positive and have a value ranging from 0 to 3 subject to the limitation that (d+e)=3, wherein the oxirane or oxetane compound is a siloxane having the formula:

$$M^E{}_hD_k$$

wherein
$M^{E=R12}R^{13}(R^E)SiO_{1/2}$
$D=R^{18}R^{19}SiO_{2/2}$
where $R^{12}$, $R^{13}$, $R^{18}$, and $R^{19}$ are methyl groups,
$R^E$ is —$(CH_2)_3OCH_2CH(O)CH_2$
subscript h is 2 and subscript k is 50.

38. The method for treating thermally damaged hair of claim 37 wherein the composition is an emulsion composition comprising a continuous phase which comprises the reaction product of (a) and (b), and a discontinuous phase which comprises water or a non-aqueous hydroxylic solvent.

39. The method for treating thermally damaged hair of claim 37 wherein the composition is an emulsion composition comprising a discontinuous phase which comprises the reaction product of (a) and (b) and a continuous phase which comprises water or a non-aqueous hydroxylic solvent.

40. The composition of claim 1 wherein the amino silane has the formula:

$$N(H)(R^1)(R^2Si(OR^4)_a$$

wherein
$R^1$ is H,
$R^2$ is —$(CH_2)_3$,
$R^4$ is —$CH(CH_3)_2$,
subscript a is 3.

* * * * *